(12) United States Patent
Dairoku et al.

(10) Patent No.: US 7,250,459 B2
(45) Date of Patent: Jul. 31, 2007

(54) ABSORBENT RESIN COMPOSITION

(75) Inventors: Yorimichi Dairoku, Hyogo (JP); Kinya Nagasuna, Hyogo (JP); Yoshihiko Masuda, Hyogo (JP); Nobuyuki Harada, Osaka (JP); Yoshihiro Motono, Hyogo (JP); Kunihiko Ishizaki, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 197 days.

(21) Appl. No.: 11/228,332

(22) Filed: Sep. 19, 2005

(65) Prior Publication Data

US 2006/0025536 A1  Feb. 2, 2006

Related U.S. Application Data

(62) Division of application No. 10/229,111, filed on Aug. 28, 2002, now Pat. No. 6,992,144, which is a division of application No. 08/747,828, filed on Nov. 13, 1996, now abandoned, which is a division of application No. 08/388,838, filed on Feb. 15, 1995, now Pat. No. 5,610,208.

(30) Foreign Application Priority Data

Feb. 17, 1994 (JP) .................................... 6-20295
Mar. 22, 1994 (JP) .................................... 6-50365

(51) Int. Cl.
C08K 5/09 (2006.01)

(52) U.S. Cl. .................. 524/322; 524/284; 524/321; 524/556; 524/560; 524/561

(58) Field of Classification Search ............. 524/284, 524/321, 322, 556, 560, 561
See application file for complete search history.

(56) References Cited

U.S. PATENT DOCUMENTS

| | | | |
|---|---|---|---|
| 3,926,891 A | 12/1975 | Gross et al. | |
| 3,966,679 A | 6/1976 | Gross | |
| 4,102,340 A | 7/1978 | Mesek et al. | |
| 4,190,563 A | 2/1980 | Bosley et al. | |
| 4,446,261 A | 5/1984 | Yamasaki et al. | |
| 4,497,930 A | 2/1985 | Yamasaki et al. | |
| 4,654,039 A | 3/1987 | Brandt et al. | |
| 4,666,983 A | 5/1987 | Tsubakimoto et al. | |
| 4,721,647 A | 1/1988 | Nakanishi et al. | |
| 4,734,478 A | 3/1988 | Tsubakimoto et al. | |
| RE32,649 E | 4/1988 | Brandt et al. | |
| 4,783,510 A | 11/1988 | Saotome | |
| 4,806,578 A | 2/1989 | Kobayashi et al. | |
| 4,822,453 A | 4/1989 | Dean et al. | |
| 4,910,250 A | 3/1990 | Saotome | |
| 5,032,628 A | 7/1991 | Choi et al. | |
| RE33,839 E | 3/1992 | Miroslav et al. | |
| 5,115,011 A | 5/1992 | Harada et al. | |
| 5,137,537 A | 8/1992 | Herron et al. | |
| 5,140,076 A | 8/1992 | Hatsuda et al. | |
| 5,229,488 A | 7/1993 | Nagasuna et al. | |
| 5,298,570 A | 3/1994 | Tahara et al. | |
| 5,322,896 A | 6/1994 | Ueda et al. | |
| 5,326,819 A | 7/1994 | Kanbayashi et al. | |
| 5,331,059 A | 7/1994 | Engelhardt et al. | |
| 5,382,610 A | 1/1995 | Harada et al. | |
| 5,422,405 A | 6/1995 | Dairoku et al. | |
| 5,447,727 A | 9/1995 | Graham | |
| 5,451,613 A | 9/1995 | Smith et al. | |
| 5,462,972 A | 10/1995 | Smith et al. | |
| 5,475,062 A | 12/1995 | Ishizaki et al. | |
| 5,478,879 A | 12/1995 | Kajikawa et al. | |
| 5,494,940 A | 2/1996 | Unger et al. | |
| 5,502,082 A | 3/1996 | Unger et al. | |
| 5,541,234 A | 7/1996 | Unger et al. | |
| 5,610,208 A | 3/1997 | Dairoku | |
| 5,610,220 A | 3/1997 | Klimmek et al. | |
| 5,614,570 A | 3/1997 | Hansen et al. | |
| 6,716,894 B2 | 4/2004 | Kajikawa et al. | |

FOREIGN PATENT DOCUMENTS

| | | |
|---|---|---|
| EP | 0009977 A1 | 4/1980 |
| JP | 62-149336 A | 7/1987 |
| JP | 03-195705 A | 8/1991 |
| JP | 04-120176 A | 4/1992 |
| WO | WO 94/15651 A1 | 7/1994 |

*Primary Examiner*—Bernard Lipman
(74) *Attorney, Agent, or Firm*—Buchanan Ingersoll & Rooney PC

(57) ABSTRACT

A method for the production of a water-absorbent agent comprises mixing an absorbent resin containing a carboxyl group with an additive soluble in the aqueous solution of at least one member selected from the group consisting of inorganic acids, organic acids, and polyamino acids and a cross-linking agent capable of reacting with the carboxyl group. A water-absorbent agent obtained by adding from 0.005 to 8 parts by weight of an epoxy compound to 100 parts by weight of a water-absorbent resin, exhibiting an absorption capacity without load of at least 45 (g/g), an absorption capacity under load of 20 $g/cm^2$ of not less than 30 (ml/g) and having a residue amount of an epoxy compound of not more than 2 ppm. A water-absorbent composition comprises a polyamino acid (salt) and a water-absorbent resin containing a carboxyl group.

11 Claims, 1 Drawing Sheet

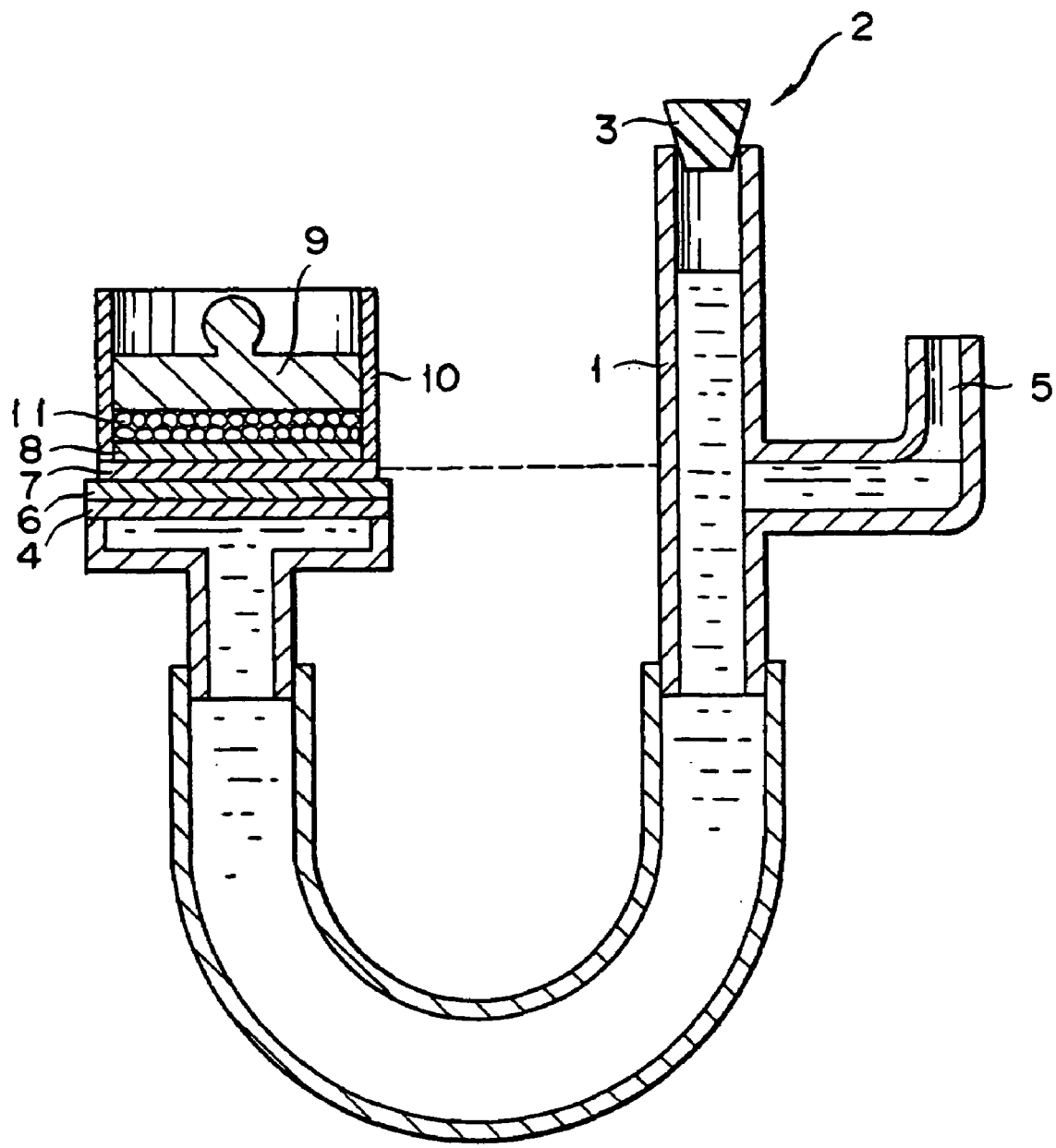
FIGURE

ABSORBENT RESIN COMPOSITION

CROSS-REFERENCE TO RELATED APPLICATIONS

This application is a divisional of application Ser. No. 10/229,111, filed Aug. 28, 2002, now U.S. Pat. No. 6,992,144, in turn a divisional of application Ser. No. 08/747,828, filed Nov. 13, 1996, now abandoned, in turn, a divisional of application Ser. No. 08/388,838, filed Feb. 15, 1995, now U.S. Pat. No. 5,610,208, the contents of which are incorporated herein by reference, which in turn claims priority to Japanese application Nos. 6-20295 and 6-50365, filed Feb. 17, 1994 and Mar. 22, 1994, respectively.

BACKGROUND OF THE INVENTION

1. Field of the Invention

This invention relates to a water-absorbent agent, a method for the production thereof, and a water-absorbent composition. More particularly, it relates to a water-absorbent agent manifesting as high an absorption capacity even under load as without load, excelling in safety as evinced by the absence from the resin surface of a residue of the cross-linking agent of high reactivity, and befitting sanitary materials and to a method for the production thereof. It also relates to a novel water-absorbent composition which exhibits an excellent water-absorbent property to such body liquid as urine, blood, and secretions, enjoys unusual gel stability, and also excels in the flowability after absorbing moisture, the ability to resist static charge, and the rustproofing effect.

2. Description of the Prior Art

In recent years, the water-absorbent resins have been in extensive use as one of the component materials of such sanitary materials as disposable diapers and sanitary napkins for the purpose of absorbing body liquid.

The water-absorbent resins of this class heretofore known to the art include partially neutralized cross-linked polyacrylic acids (JP-A-55-84,304, JP-A-55-108,407, JP-A-55-133,413, U.S. Pat. No. 4,654,039, and U.S. Pat. No. 4,286,082), hydrolyzed starch-acrylonitrile graft polymers (JP-A-46-43,995 and U.S. Pat. No. 3,661,815), neutralized starch-acrylic acid graft polymers (JP-A-51-125,468 and U.S. Pat. No. 4,076,663), saponified vinyl acetate-acrylic ester copolymers (JP-A-52-14,689 and U.S. Pat. No. 4,124,748), hydrolyzed acrylonitrile copolymers or acrylamide copolymers (JP-A-53-15,959, U.S. Pat. No. 3,935,099 and U.S. Pat. No. 3,959,569), cross-linked derivatives thereof, cross-linked carboxymethyl cellulose (U.S. Pat. No. 4,650,716 and U.S. Pat. No. 4,689,408, and cross-linked polymer of cationic monomers (JP-A-58-154,709, JP-A-58-154,710, U.S. Pat. No. 4,906,717, U.S. Pat. No. 5,075,399, and EP0304143), cross-linked isobutylene-maleic anhydrous copolymers (U.S. Pat. No. 4,389,513), and cross-linked copolymers of 2-acrylamide-2-methylpropanesulfonic acid with acrylic acid (EP068189), for example.

The characteristic qualities which the water-absorbent resins are desired to possess include high water-absorption capacity and fine speed of absorption to be manifested on contract with aqueous liquids, liquid permeability, high strength exhibited by the gel swelled with liquid, and ability to aspirate water from the substrate impregnated with aqueous liquid, for example. These qualities are not necessarily correlated positively to one another. For example, such physical properties as the liquid permeability, the gel strength, and the absorption speed are lowered in proportion as the water-absorption capacity is heightened.

As a measure to improve the various water-absorption properties of the water-absorbent resins in finely balanced levels, the technique of cross-linking the surface regions of water-absorbent resin particles has been known. Various methods have been heretofore proposed concerning the technique.

For example, methods using polyhydric alcohols (JP-A-58-180,233, JP-A-61-16,903, U.S. Pat. No. 4,734,478, and U.S. Pat. No. 5,164,459), a method using polyglycidyl compounds, polyadiridine compounds, polyamine compounds, and polyisocyanate compounds (JP-A-59-189,103), methods using glyoxal (JP-A-52-117,393 and U.S. Pat. No. 4,051,086), methods using polyvalent metals (U.S. Pat. No. 4,043,952, JP-A-51-136,588, JP-A-61-257,235, and JP-A-62-7,745), methods using a silane coupling agent (U.S. Pat. No. 4,755,560, JP-A-61-211,305, JP-A-61-252,212, and JP-A-61-264,006), a method using a monoepoxy compound (JP-A-61-098,121), a method using an epoxy group-containing polymeric compound (U.S. Pat. No. 4,758,617), a method using an epoxy compound and a hydroxy compound (JP-A-02-132,103), and a method using an alkylene carbonate (DE-4020780) severally as a cross-linking agent have been known. Besides, methods requiring the presence of an inactive inorganic powder (JP-A-60-163,956, JP-A-60-255,814, and U.S. Pat. No. 4,587,308), a method requiring the presence of a dihydric alcohol (JP-A-01-292,004), a method requiring the presence of water and an ether compound (JP-A-02-153,903), and a method the presence of the alkylene oxide adduct of a monohydric alcohol, an organic acid salt, lactam, etc. (EP-0555692) in the process of a cross-linking reaction have been known.

These methods indeed improve the balances of the various physical properties of the absorbent resins. The degrees of these improvements, however, hardly deserve to be rated fully satisfactory. Thus, the water-absorbent resins have room for further improvement in qualities. Particularly, in recent years, the desirability of perfecting a water-absorbent resin which is capable of exhibiting outstanding water-absorption properties under load, especially water-absorption capacity under load while keeping at a high level the water-absorption capacity without load, i.e. one of the basic physical properties of the conventional water-absorbent resins, has been finding popular recognition. Of course, the water-absorption capacity without load and the water-absorption capacity under load are generally in a contradicting relation. With all the methods heretofore known to the art, the needs of further technical improvements have not been fully satisfied.

Besides, the water-absorbent resins have the problem of requiring use of a cross-linking agent in cross-linking the surface region of water-absorbent resin particles and inevitably suffering this cross-linking agent to persist as a residue on the surface of resin particles. This problem is absent when the cross-linking agent so used has low reactivity and high safety as in the case of a polyhydric alcohol. When the cross-linking agent has high reactivity as in the case of an epoxy compound, though the cross linking in the surface region proceeds quickly and, the fact remains that the cross-linking agent itself has the nature of irritating the skin and, when suffered to persist on the surface of resin, jeopardizing the safety of sanitary materials using the cross-linked absorbent resin. This gives rise to a new problem from the viewpoint of safety.

The method which, for the purpose of decreasing the amount of the fraction of a cross-linking agent being used for cross-linking the surface region which persists as a residue in the resin, comprises initiating the cross-linking reaction of the surface region of resin at a specific water content and adding a specific amount of water to the cross-linking reaction system while the reaction is in progress has been known (JP-A-03-295,705). This method, however, not only entails a complicated process but also fails to decrease the amount of a residue of the cross-linking agent sufficiently.

The methods described above fulfill, though not thoroughly, the improvement of the balances of various physical properties of water-absorbent resins and the enhancement of the absorption capacity of the water-absorbent resins under load. They at times prove undesirable from the viewpoint of safety because the cross-linking agent used for cross-linking the surface region of the water-absorbent resins particles possibly leaves behind a persistent residue in the polymer.

They have further problems of low flowability (blocking) with the high hygroscopicity of the produced water-absorbent resins itself which renders difficult the work of fabricating the water-absorbent resins under the conditions of high temperature and high humidity, the susceptibility of the water-absorbent resins to static charging which degrades the ease of handling, and the ability of the water-absorbent resins to gather rust on metal which induces corrosion of the devices to be used for the work of fabrication. Further, when the liquid to be absorbed is blood, the absorption capacity of the water-absorbent resins is degraded because the blood components of the blood being absorbed by the water-absorbent resins envelope the individual water-absorbent resins particles and eventually obstructing them from continuing their function as a water-absorbent. The water-absorbent resins heretofore known have not been always given fully satisfactory results particularly in such applications as sanitary napkins, for example.

Then a method which attains the purpose of improving the water-absorbing power of water-absorbent resins relative to blood by adding such compounds as common salt and polyether to the water-absorbent resins has been proposed (JP-A-58-501,107, JP-A-55-50,357, JP-A-54-70,694, US-Re 33839, EP-A-0009977, U.S. Pat. No. 4,190,563, etc.). Indeed, this method is effective to some extent in preventing the individual water-absorbent resins particles from conglomeration, it actually cannot bring about the expected effect because the added compound either degrades the water-absorbent resins' own absorption capacity or fails to increase the suction power to blood.

An object of this invention, therefore, is to provide an absorbent agent manifesting as high an absorption capacity even under load as without load, excelling in safety as evinced by the absence from the resin surface of a residue of the cross-linking agent of high reactivity, and befitting sanitary materials and to a method for the production thereof.

Another object of this invention is to provide a novel water-absorbent composition, wherein a water-absorption capacity, especially an absorption property to blood is sufficient and workability and safety are satisfied, a method for the production thereof, and a water-absorbent structure and a water-absorbent article both containing the water-absorbent composition.

The water-absorbent composition of this invention is adapted for disposable diapers, sanitary napkins, jigs for use on patients of incontinence, such water-absorbent articles as injury protecting materials and injury curing materials which serve the purpose of absorbing body liquid, or biotechnology applications.

SUMMARY OF THE INVENTION

The inventors, as a result of a diligent study pursued for accomplishing the objects mentioned above, have found that when a specific additive is used in the production of a water-absorbent agent by mixing a water-absorbent resin containing a carboxyl group with a cross-linking agent capable of reacting with the carboxyl group, the water-absorbent agent exhibiting a preeminently excellent water-absorption capacity under load while retaining various absorption qualities, particularly water-absorption capacity without load, at high levels and, even when the cross-linking agent has high reactivity, suppressing notably the amount of a residue of the cross-linking agent is easily obtained and that a specific water-absorbent composition is remarkably superior in absorption of blood. This invention has been perfected on the basis of this knowledge.

The various objects described above are accomplished by a method for the production of a water-absorbent agent which comprises mixing a water-absorbent resin containing a carboxyl group with an additive soluble in an aqueous solution of at least one member selected from the group consisting of inorganic acids, organic acids, and polyamino acids and a cross-linking agent capable of reacting with the carboxyl group.

This invention also concerns the method which comprises mixing the water-absorbent resin with the additive and the cross-linking agent and subsequently subjecting the mixture to a heat treatment at a temperature in the range of from 100° to 230° C. This invention also concerns the method which comprises preparatorily mixing the additive and the cross-linking agent and subsequently adding the mixture to the water-absorbent resin. This invention also concerns the method, wherein the additive is at least one member selected from the group consisting of saturated organic carboxylic acids, saturated inorganic acids of elements of Group 3 in the periodic table of elements, and poly(monoaminodicarboxylic acids). This invention also concerns the method, wherein the absorbent resin containing a carboxyl group is obtained by polymerizing a hydrophilic monomer having acrylic acid and/or a salt thereof as a main component thereof. This invention also concerns the method, wherein the cross-linking agent capable of reacting with the carboxylic group is an epoxy compound. This invention also concerns the method, wherein the acid dissociation index (pKa value) of the additive is in the range of from 2.0 to 4.0. This invention also concerns the method, wherein the additive is a saturated organic carboxylic acid. This invention also concerns the method, wherein the saturated organic carboxylic acid is at least one compound selected from the group consisting of citric acid, succinic acid, and lactic acid. This invention also concerns the method, wherein the mixing is effected by the use of from 0.01 to 5 parts by weight of water based on 100 parts by weight of the absorbent resin. This invention also relates to the method, wherein the water-absorbent resin comprises irregular broken particles of an average particle diameter of from 200 to 600 μm and includes not more than 10% by weight of a fraction of particles of less than 150 μm in diameter. This invention also concerns the method, wherein the additive is used at a ratio in the range of from 0.01 to 5 parts by weight to 100 parts by weight of the water-absorbent resin. This invention also relates to the method, wherein the water-absorbent resin has a water content in the range of from 1 to 10%.

The objects mentioned above are further accomplished by a water-absorbent agent obtained by adding from 0.005 to 8 parts by weight of an epoxy compound to 100 parts by weight of a water-absorbent resin containing carboxyl group, exhibiting an absorption capacity without load of not less than 45 (g/g) and an absorption capacity under a load of 20 g/cm$^2$ of not less than 30 (ml/g) and having a residue amount of an epoxy compound of not more than 2 ppm.

This invention also concerns the water-absorbent agent, wherein a hydroxyl group-containing saturated organic acid is contained at a concentration in the range of from 0.01 to 5% by weight (based on the water-absorbent resin). This invention also concerns the water-absorbent agent, wherein the absorption capacity under load of 20 g/cm$^2$ is not less than 35 (ml/g) and the epoxy compound is no longer detected.

The objects mentioned above are further accomplished by a water-absorbent composition comprising a polyamino acid (salt thereof) and a water-absorbent resin containing a carboxyl group.

This invention also concerns the composition, wherein the water-absorbent resin is a cross-linked polymer of acrylic acid (salt). This invention also concerns the composition, wherein the ratio of the polyamino acid (salt) is from 0.01 to 30 parts by weight to 100 parts by weight of the water-absorbent resin. This invention also concerns the composition, wherein the polyamino acid (salt) is at least one member selected from the group consisting of polyaspartic acid (salt), polyglutamic acid (salt), and polylysine (salt).

The various objects are further accomplished by a water-absorbent composition comprising a water-absorbent resin exhibiting an absorption capacity of at least 25 g/g to physiological saline solution without load and a suction power of not less than 14 g/g to physiological saline solution and a suction power of at least 7 g/g to bovine blood.

The various objects are further accomplished by a water-absorbent structure comprising 10 to 95 parts by weight of a water-absorbent composition containing a polyamino acid (salt) and a water-absorbent resin having a carboxyl group and 90 to 5 parts by weight of a hydrophilic fibers. This invention also concerns the water-absorbent structure which further comprises up to 40 parts by weight of a thermoplastic fibers. This invention also concerns the water-absorbent structure, wherein the density is in the range of from 0.06 to 0.5 g/cc.

The various objects are further accomplished by a water-absorbent structure comprising 50 to 95 parts by weight of a water-absorbent composition formed of a water-absorbent resin exhibiting an absorption capacity of at least 25 g/g to physiological saline solution without load and a suction power of not less than 14 g/g to physiological saline solution and a suction power of at least 7 g/g to bovine blood and 50 to 5 parts by weight of a hydrophilic fibers. This invention also concerns the water-absorbent structure, which further comprises up to 40 parts by weight of thermoplastic fibers based on 100 parts by weight of the hydrophilic fibers. This invention also concerns the water-absorbent structure, wherein the density is in the range of from 0.06 to 0.5 g/cc.

The various objects are further accomplished by a water-absorbent article furnished with the water-absorbent structure mentioned above and/or the water-absorbent composition mentioned above.

The method of this invention permits easy and convenient manufacture of a water-absorbent agent which exhibits as high an absorption capacity even under load as without load, excels in safety, and befits sanitary materials.

The water-absorbent agent of this invention exhibits a high absorption capacity without load and a very high absorption capacity under load, allows no occurrence on the resin surface of a residue of a cross-linking agent of high reactivity, permits high diffusion of liquid, and does not readily migrate in or exfoliate from pulp and, therefore, is advantageously adapted for such absorbent articles as disposable diapers and sanitary napkins and other sanitary materials.

The operation and the effect of the polyamino acid (salt) in the water-absorbent composition of this invention have not yet been fully elucidated. It has no problem from the viewpoint of safety and hygiene. The polyamino acid (salt), when added in a small amount to the water-absorbent resins, enables the quality of the water-absorbent resins to be conspicuously enhanced. The water-absorbent composition of this invention, therefore, is advantageously adapted for disposable diapers, sanitary napkins, jigs for use on patients of incontinence, such water-absorbent articles as injury protecting materials and injury curing materials which serve the purpose of absorbing body liquid, or biotechnology applications. Thus, this invention contributes immensely to the growth of the industry concerned.

BRIEF DESCRIPTION OF THE DRAWING

FIGURE is a cross section of a device used in this invention for the measurement of absorption capacity under load.

EXPLANATION OF PREFERRED EMBODIMENT

The carboxyl group-containing water-absorbent resin useful for this invention is a well-known resin which is obtained, for example, by polymerizing a hydrophilic monomer having an acrylic acid or a salt thereof as a main component and which, on exposure to water, absorbs a large volume of water, preferably absorbs physiological saline without load in an amount of 10 to 100 times and forms a substantially water-insoluble hydrogel. The water-absorbent resins of this class include partially neutralized cross-linked polymers of polyacrylic acid (U.S. Pat. No. 4,625,001, U.S. Pat. No. 4,654,039, U.S. Pat. No. 5,250,640, U.S. Pat. No. 5,275,773, EP-A-456136, etc.), a cross-linked partially neutralized starch-acrylic acid graft polymer (U.S. Pat. No. 4,076,663), a cross-linked isobutylene-maleic acid copolymer (U.S. Pat. No. 4,389,513), a saponified vinyl acetate-acrylic acid ester copolymer (U.S. Pat. No. 4,124,748), a hydrolyzed acrylamide (co)polymer (U.S. Pat. No. 3,959,569), and a hydrolyzed acrylontrile polymer (U.S. Pat. No. 3,935,099), cross-linked carboxymethyl cellulose (U.S. Pat. No. 4,650,716 and U.S. Pat. No. 4,689,408), for example. Among other water-absorbent resins cited above, the cross-linked polymer of a polyacrylic acid salt proves particularly desirable. The cross-linked polymer of the polyacrylic acid is preferable to be such that 50 to 90 mol % of the acid group in the polymer is neutralized. As typical examples of the salt, alkali metal salts, ammonium salts, and amine salts may be cited.

When the water-absorbent resin is obtained by polymerizing a hydrophilic monomer having acrylic acid and/or a salt thereof as a main component thereof, for example, the acrylic acid or the salt thereof may be copolymerized with other monomer (U.S. Pat. No. 5,338,810 and EP-0574260). As typical examples of the monomer usable for the copolymerization, anionically unsaturated monomers such as methacrylic acid, maleic acid, β-acryloyloxy propionic acid, vinyl sulfonic acid, styrene sulfonic acid, 2-(meth)acrylamide-2-methyl propanesulfonic acid, 2-(meth)acryloyl ethanesulfonic acid, and 2-(meth)acryloyl propanesulfonic acid and salts thereof; nonionic hydrophilic group-containing unsaturated monomers such as acrylamide, methacrylamide, N-ethyl(meth)acrylamide, N-n-propyl (meth)acrylamide, N-isopropyl(meth)acrylamide, N,N-dimethyl (meth) acrylamide, 2-hydroxyethyl(meth)acrylate, 2-hydroxypropyl (meth)acrylate, methoxy polyethylene glycol (meth)acrylate, polyethylene glycol mono(meth)acrylate, vinyl pyridine, N-vinyl pyrrolidone, N-acryloyl piperidine, and N-acryloyl pyrrolidine; and cationically unsaturated monomers such as N,N-dimethyl amino-ethyl (meth)acrylate, N,N-diethyl aminoethyl(meth)acrylate, N,N-dimethyl aminopropyl (meth) acrylate, N,N-dimethyl aminopropyl (meth)acrylamide, and quaternary salts thereof may be cited. The amount of the monomer to be used is generally in the range of from 0 to 50 mol %, preferably from 0 to 30 mol %, most preferably from 0 to 10 mol %, based on the amount of all the components monomers for the copolymerization.

As the water-absorbent resin for use in this invention, although it has a cross-linking structure, the water-absorbent resin obtained by the copolymerization or the reaction using an inner cross-linking agent having not less than two polymerizing unsaturated groups or not less than two reacting groups or both of polymerizing unsaturated group and reactive group is more preferable than the absorbent resin of the self-cross-linking type which has no use for a cross-linking agent.

As typical examples of the inner cross-linking agent, N,N'-methylene-bis(meth)acrylamide, (poly)-ethylene glycol di(meth) acrylate, (poly)propylene glycol di(meth)acrylate, trimethylol-propane tri(meth)acrylate, trimethylolpropane di(meth) acrylate, glycerol tri(meth)acrylate, glycerol acrylate methacrylate, ethylene oxide-modified trimethylol propane tri(meth)acrylate, pentaerythritol tetra(meth)acrylate, dipentaerythritol hexa(meth)acrylate, triallyl cyanurate, triallyl isocyanurate, triallyl phosphate, triallyl amine, poly (meth)allyloxy alkane, (poly)ethylene glycol diglycidyl ether, glycerol diglycidyl ether, ethylene glycol, polyethylene glycol, propylene glycol, glycerol, pentaerythritol, ethylene diamine, polyethylene imine, ethylene carbonate, and glycidyl(meth)acrylate may be cited. These internal cross-linking agents, when necessary, may be used in the form of a combination of two or more members. From the viewpoint of the water-absorption characteristics of the produced water-absorbent resin, it is particularly preferable to use essentially a compound having not less than two polymerizable unsaturated groups as an inner cross-linking agent. The amount of the inner cross-linking agent to be used is preferable to be in the range of from 0.005 to 2 mol %, preferably from 0.01 to 1 mol %, based on the monomer components mentioned above.

The monomers to be polymerized may incorporate therein a hydrophilic polymeric compound such as starch or cellulose, starch derivatives or cellulose derivatives, polyvinyl alcohol, polyacrylic acid (salt), or cross-linked polyacrylic acid (salt), a chain transfer agent such as hypophosphorous acid (salt), surfactants, and foaming agents such as carbonates, etc.

The compounds for addition to these monomers are disclosed in U.S. Pat. No. 4,076,663, U.S. Pat. No. 4,286,082, U.S. Pat. No. 4,320,040, U.S. Pat. No. 4,833,222, U.S. Pat. No. 5,118,719, U.S. Pat. No. 5,149,750, U.S. Pat. No. 5,154,713, U.S. Pat. No. 5,264,495, EP-A-03729831, and EP-A-0496594, for example.

In the polymerization of the monomer for the production of the water-absorbent resin for use in this invention, though bulk polymerization or precipitation polymerization is available, it is preferable to prepare the monomer in the form of an aqueous solution and subjecting the aqueous solution to solution polymerization or reversed-phase suspension polymerization from the viewpoint of the quality of product and the ease of control of polymerization. Concentration of the aqueous solution is in the range of from 10 to 70% by weight, preferably from 20% by weight to a saturated concentration.

Such polymerization methods are described in, for example, U.S. Pat. No. 4,625,001, U.S. Pat. No. 4,769,427, U.S. Pat. No. 4,873,299, U.S. Pat. No. 4,093,776, U.S. Pat. No. 4,367,323, U.S. Pat. No. 4,446,261, U.S. Pat. No. 4,552,938, U.S. Pat. No. 4,654,393, U.S. Pat. No. 4,683,274, U.S. Pat. No. 4,690,996, U.S. Pat. No. 4,721,647, U.S. Pat. No. 4,738,867, U.S. Pat. No. 4,748,076, U.S. Pat. No. 4,985,514, U.S. Pat. No. 5,124,416, U.S. Pat. No. 5,247,225 and U.S. Pat. No. 5,250,640.

The polymerization may be initiated by the use of a radical polymerization initiator such as potassium persulfate, ammonium persulfate, sodium persulfate, t-butyl hydroperoxide, hydrogen peroxide, or 2,2'-azo-bis-(2-amidinopropane) dihydrochloride or by dint of an active energy radiation such as ultraviolet light or an electron ray, but it is preferable to use the radical polymerization initiator. When an oxidizing radical polymerization initiator is used, such a reducing agent as sodium sulfite, sodium hydrogen sulfite, ferric sulfate, or L-ascorbic acid (salt) may be additionally used to effect redox polymerization. These polymerization initiators and reducing agents may be used in two kinds or more, and an amount thereof to be used is generally in the range of from 0.001 to 2 mol %, preferably from 0.01 to 0.5 mol % based on the monomer.

The gel polymer which results from the polymerization is preferably dried. This drying may be effected by any of the known methods such as hot air drying, drying with specific steam (U.S. Pat. No. 4,920,202), microwave drying (U.S. Pat. No. 5,075,344), infrared drying, vacuum drying, drying by means of a drum drier, and azeotropic dehydration in a hydrophobic organic solvent. The drying is effected at a temperature in the range of from 70° to 300° C., preferably from 100° to 250° C. The gel polymer may be finely divided prior to the drying by the method disclosed in U.S. Pat. No. 5,275,773. The supply of the gel polymer to the drier may be controlled by the method taught in U.S. Pat. No. 5,229,487.

To be used advantageously for this invention, the water-absorbent resin obtained by the polymerization described above assumes the shape of irregular broken particles, beads, sheets, fibers, rods, and rough spheres. For the purpose of obtaining a water-absorbent agent which manifests the effect of the invention to the fullest possible extent and exhibits high absorption capacity under load as without load and excels in safety owing to the absence of an unaltered residue of a cross-linking agent, it is preferable to use as the starting raw material spherical or irregular broken water-absobent resin, most preferably a water-absorbent resin which is obtained by the polymerization of an aqueous solution of a monomer and which comprises irregular broken particles of an average particle diameter of from 200 to 600 μm and includes not more than 10% by weight of a fraction of particles of less than 150 μm in diameter. If the average particle diameter is less than 200 μm, the absorption capacity under load possibly will not be easily improved. Conversely, if it exceeds 600 μm, possibly the speed of absorption will be unduly low and the saturation of absorption will take an unduly long time. It should be noted that if the amount of the fraction of resin having particle diameters of less than 150 µm exceeds 10% by weight, the decrease of the amount of a residue of the cross-linking agent possibly will not be easily attained.

The water-absorbent resin to be used in this invention can be handled as a powder when it has a water content in the range of from 1 to 50%, desirably from 1 to 20%, and more preferably from 1 to 10% after the resin resulting from polymerization has been dried as occasion demands. If the water content exceeds 50%, the cross-linking agent to be used in this invention will permeate the water-absorbent resin particles thoroughly to the cores and, in spite of the use of the at least one additive selected from the group consisting of inorganic acids, organic acids, and polyamino acids, the absorption capacity will be degraded and the absorption characteristics under load possibly will not be improved.

The additive to be used in this invention has no particular restriction except for the requirement that it be an inorganic acid and/or an organic acid and/or a polyamino acid which is soluble in an aqueous liquid. The term "aqueous liquid" as used herein refers to water and a mixture of water with a hydrophilic organic solvent. Only naturally, the substances which have pKa values exceeding 7.0 and, therefore, are uniquely recognized as basic compounds or salts by persons of ordinary skill in the art do not belong to the inorganic or the organic acids mentioned above.

The term "organic acids" as used in this invention refers to acidic compounds which are formed of carbon, hydrogen, and oxygen elements and are represented by organic carboxylic acids, organic sulfonic acids, and organic sulfinic acids. Among organic acids cited above, the organic carboxylic acids prove particularly preferable. Further, in all the organic carboxylic acids, saturated organic carboxylic acids prove desirably and hydroxy group-containing saturated organic carboxylic acids prove particularly preferable.

Then, the term "inorganic acids" refers to acidic compounds which are formed of inorganic substances and hydrogen elements. The inorganic substances are desired to be inorganic acids of elements of Group 3 in the Periodic Table of Element inclusive essentially of at least one member of phosphorus, sulfur, and chlorine, preferably saturated inorganic acids of elements of Group 3 in the Periodic Table of Elements. The term "saturated inorganic acids" as used in this invention refers to inorganic acids having relevant inorganic substances in the most stable state of oxidation where the inorganic substances are capable of assuming a plurality of states of oxidation. The inorganic acids which contain phosphorus of the positive pentavalent (+5) form, sulfur of the positive hexavalent (+6) form, and chlorine of the negative monovalent (−1) form are examples.

As concrete examples of the additive described above, inorganic acids such as pyrophoshoric acid tripolyphosphoric acid, phosphoric acid, sulfuric acid, and hydrochloric acid and organic acids such as anisic acid, benzoic acid, formic acid, valeric acid, citric acid, glyoxylic acid, glycolic acid, glycerin phosphoric acid, glutaric acid, chloroacetic acid, chloropropionic acid, cinnamic acid, succinic acid, acetic acid, tartaric acid, lactic acid, pyruvic acid, fumaric acid, propionic acid, 3-hydroxypropionic acid, malonic acid, butyric acid, isobutyric acid, imidinoacetic acid, malic acid, isothionic acid, citraconic acid, adipic acid, itaconic acid, crotonic acid, oxalic acid, salicylic acid, gluconic acid, gallic acid, sorbic acid, gluconic acid, and p-oxybenzoic acid may be cited. If such organic or inorganic acid is substituted by a basic compound or a salt, the absorption characteristics under load will not be improved at all and the decrease of the amount of a residue of the cross-linking agent used for cross-linking the surface region will be unduly small. Further, even if the organic or inorganic salt is added prior to the polymerization, it is meaningless.

The inorganic acid and the organic acid are preferable to be such that the acid dissociation index (the pKa value which is the logarithm of the reciprocal of the acid dissociation constant) thereof in an aqueous solution may be in the range of from 2.0 to 4.0. For example, one or more members selected from the group consisting of phosphoric acid, pyrophosphoric acid, tripoly-phosphoric acid, citric acid, succinic acid, and lactic acid are favorably used. In all the additives which have acid dissociation indexes (pKa values) in the range of from 2.0 to 4.0, and among them, organic acids prove preferable. Further, a molecular weight of the organic acids and inorganic acids are preferable in the range of 30 to 1000, more preferably 60 to 500. Among the above-mentioned saturated organic acids and inorganic acids of elements of Group 3 in the Periodic Table of Element, such saturated organic carboxlic acids as succinic acid, citric acid, and lactic acid, especially hydroxyl group-containing saturated organic carboxylic acids prove more preferable. The acid dissociation index is described in Basic Volume, Chemical Handbook, 3rd edition, pp. II-337 to 342, published by Maruzen Book Co., Ltd. and the pieces of literature indicated in the footnote thereof.

In the surface cross-linkage contemplated by this invention, a polyamino acid is favorably used besides the organic acid and the inorganic acid described above to accomplish the desire to decrease the amount of a residue of the cross-linking agent and improve the absorption capacity under load. From the viewpoint of effective reduction of the amount of a residue of the cross-linking agent which constitutes one of the objects of this invention, the saturated organic carboxylic acids mentioned above excel polyamino acids. The essential use of a polyamino acid, however, brings about prominent effects of notably improving the absorbent resin's ability to absorb blood, etc., as will be described specifically afterward, separately of the effect of the inorganic and the organic acid.

As examples of the polyamino acid usable effectively in this invention, homopolymers of at least dimeric order and copolymers which have such α-amino acids, β-amino acids, and γ-amino acids as aspartic acid and lysine coupled through the medium of peptide bonds, without reference particularly to distinction between the D form and the L form, may be cited. More specifically, polyglycine, polyalanine, polyvaline, poly-leucine, polyisoleucine, polyphenylalanine, polythyrosin, poly-oxyproline, polyproline, polyserine, polythreonine, polythyrosin, polycystein, polycystine, polymethionine, polytryptophan, poly-aspartic acid, polyglutamic acid, polylysine, polyarginin, polyhistidine and copolymers thereof may be cited. Among other polyamino acids (salts) cited above, poly(monoaminodicarboxylic acids) such as polyaspartic acid and polyglutamic acid prove most preferable, and these carboxylic group and amino group may be partially converted into salts. As respects the molecular weight of the polyamino acid which is usable in this invention, those polyamino acids (salts) of relatively low molecular weights of the levels of dimers, desirably pentamers, and more desirably decamers or the like otherwise called polypeptides up to those polyamino acids (salts) of very high molecular weights of several millions can be advantageously used. The molecular weight is desired to be in the approximate range of from 100 to 1,000,000, preferably from 1,000 to 500,000.

The amount of the additive to be used in this invention is generally in the range of from 0.005 to 8 parts by weight, preferably from 0.01 to 5 parts by weight, based on 100 parts by weight of the solids of the water-absorbent resin, though variable with the cross-linking agent to be used for cross-linking the surface region of the absorbent resin particles. If this amount exceeds 8 parts by weight, the excess will neither bring about any economic benefit nor contribute to the accomplishment of the optimum effect of cross-linkage aimed at by this invention. Conversely, if the amount is less than 0.005 part by weight, the additive will not be fully effective in improving the absorption characteristics under load or in decreasing the amount of a residue of the cross-linking agent. The most preferable amount is in the range of from 0.1 to 3 parts by weight. In the case of a polyamino acid, the amount for effective use may be increased up to 30 parts by weight for the reason which will be described hereinafter.

The expression "cross-linking agent capable of reacting with a carboxyl group" and usable in this invention means that this cross-linking agent reacts with a carboxyl group by forming a covalent bond or an ionic bond therewith. Numerous well-known cross-linking agents in popular use answer this description. As concrete examples of the cross-linking agent, polyhydric alcohol compounds such as ethylene glycol, diethylene glycol, propylene glycol, triethylene glycol, tetraethylene glycol, polyethylene glycol, propylene glycol, 1,3-propanediol, dipropylene glycol, 2,2,4-trimethyl-1,3-pentadiol, polypropylene glycol, glycerol, polyglycerol, 2-butene-1,4-diol, 1,4-butanediol, 1,5-pentanediol, 1,6-hexanediol, 1,2-cyclohexane dimethanol, 1,2-cyclohexanol, trimethylol propane, diethanol amine, triethanol amine, polyoxypropylene, oxyethylene-oxypropylene block copolymer, pentaerythritol, and sorbitol; epoxy compounds such as ethylene glycol diglycidyl ether, polyethylene diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; polyamine compounds such as ethylene diamine, diethylene triamine, triethylene tetramine, tetraethylene pentamine, pentaethylene hexamine, polyamide polyamine, and polyethylene imine and epihalohydrin condensates with these polyamine compounds; polyisocyanate compounds such as 2,4-tolylene diisocyanate and hexamethylene diisocyanate; polyoxa-zoline compounds such as 1,2-ethylene-bis-oxazoline; silane coupling agents such as γ-glycidoxypropyl trimethoxy silane and γ-amino propryl trimethoxy silane; alkylene carbonate compounds such as 1,3-dioxolan-2-on, 4-methyl-1,3-dioxolan-2-on, 4,5-dimethyl-1,3-dioxolan-2-on, 4,4-dimethyl-1,3-dioxolan-2-on, 4-ethyl-1,3-dioxolan-2-on, 4-hydroxymethyl-1,3-dioxolan-2-on, 1,3-dioxan-2-on, 4-methyl-1,3-dioxan-2-on, 4,6-dimethyl-1,3-dioxan-2-on, and 1,3-dioxolan-2-on; haloepoxy compounds such as epichlorohydrin, epibromohydrin, and α-methyl epichlorohydrin; and polyvalent metal compounds such as hydroxides and chlorides of zinc, calcium, magnesium, aluminum, iron, and zirconium may be cited. These cross-linking agents may be used either singly or in the form of a mixture of two or more members. And among these cross-linking agents, at least one member selected from the group consisting of the polyvalent alcohols, epoxy compounds, alkylene carbonate compound, polyamine compounds and epihalohidrin condensate thereof are preferable.

For the purpose of attaining the effects of this invention to the fullest possible extent, it is desirable to use an epoxy compound as an essential component of the cross-linking agent. In this case, the effects of this invention may be manifested more conspicuously by using two or more kinds of cross-linking agents having solubility parameters in different ranges as shown in EP Application No. 93101068.5 and U.S. Ser. No. 08/167,077.

When at least two kinds of the cross-linking agents are used, a first cross-linking agent which can preferably be used in this invention is required to possess a solubility parameter (SP value) of 12.5 $(cal/cm^3)^{1/2}$ and exhibit reactivity with a carboxyl group. The solubility parameter (SP value) is used generally as a factor representing the polarity of a given compound. This invention adopts the numerical value of the solubility parameter δ $(cal/cm^3)^{1/2}$ of solvent reported in the "Polymer Handbook," third edition (Wiley Interscience Corp), VII-527 to 539. For a cross-linking agent which is not included in the table, this invention proposes to adopt the numerical value δ $(cal/cm^3)^{1/2}$ which is derived by substituting the Hoy's cohesive energy constant reported in VII-525 ibidem in the Small's formula found in VII-524 ibidem.

As typical examples of the first cross-linking agent which possesses such a solubility parameter (SP value) of not less than 12.5 $[(cal/cm^3)^{1/2}]$ and exhibits reactivity with a carboxyl group, ethylene glycol, propylene glycol, glycerol, polyglycerol, pentaerythritol, sorbitol, ethylene carbonate, propylene carbonate, etc. may be cited. One member or a mixture of two or more members selected from among these examples may be used effectively. Preferably, this solubility parameter (SP value) is in the range of 13.0 to 18.0 $(cal/cm^3)^{1/2}$.

When at least two kinds of the cross-linking agents are used, a second cross-linking agent which is effectively usable in this invention is preferable to possess a solubility parameter (SP value) of less than 12.5 $(cal/cm^3)^{1/2}$ and exhibit reactivity with a carboxyl group. As typical examples of the second cross-linking agent, diethylene glycol, triethylene glycol, tetraethylene glycol, dipropylene glycol, tripropylene glycol, 1,3-butanediol, 1,4-butane-diol, 1,5-pentanediol, 2,4-pentanediol, 1,6-hexanediol, 2,5-hexanediol, trimethylol propane, diethanolamine, triethanolamine, ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, ethylene diamine, diethylenetriamine, triethylenetetramine, 2,4-tolylene diisocyanate, hexamethylene diisocyanate, 4,5-dimethyl-1,3-dioxolan-2-on, epichlorohydrin, and epibromohydrin may be cited. One member or a mixture of two or more members selected from among these cross-linking agents can be used effectively herein. Preferably, the solubility parameter (SP value) is in the range between not less than 9.5 $(cal/cm^3)^{1/2}$ and less than 12.0 $(cal/cm^3)^{1/2}$.

When at least two kinds of the cross-linking agents are used, the selection of the first and second cross-linking agents is preferable to be such that the difference between the solubility parameter (SP value) of the first cross-linking agent and the solubility parameter (SP value) of the second cross-linking agent is not less than 2 $(cal/cm^3)^{1/2}$. If the difference of the two solubility parameters (SP values) is less than 2 $(cal/cm^3)^{1/2}$, the possibility arises that the effect to be derived from the use of these two species of cross-linking agent will not be easily manifested and the improvement of absorption properties under load will be attained with difficulty. Preferably, the selection of the first and second cross-linking agents is such that the difference of the solubility parameter (SP value) of the first cross-linking agent and the solubility parameter (SP value) of the second cross-linking agent is not less than 3 $(cal/cm^3)^{1/2}$.

The first cross-linking agent is preferable to have a molecular weight of not more than 200 and the second cross-linking agent to have a molecular weight of not more than 350. If the molecular weight of the first cross-linking agent exceeds 200, the possibility ensues that the first cross-linking agent will not permeate the particles of the absorbent resin as the base polymer deeply through the surface thereof but tend to stagnate in the surface region thereof and the absorption properties of the produced absorbent resin under load will be improved with difficulty. If the molecular weight of the second cross-linking agent exceeds 350, the possibility arises that this second cross-linking agent will only sparingly permeate the particles of the absorbent resin as the base polymer and the absorption properties of the produced absorbent resin under load will be improved only with difficulty. Preferably, the first cross-linking agent has a molecular weight in the range of 50 to 150 and the second cross-linking agent a molecular weight in the range of 150 to 300.

In the present invention, the additive is effective in optimizing the distribution of the cross-linking agent, enabling the produced absorbent agent to exhibit a high absorption capacity under load, decreasing the amount of a residue of the cross-linking agent. When an epoxy compound abounding in reactivity is used as the additive, the effect in decreasing the amount of a residue of the cross-linking agent is especially prominent. Thus, the water-absorbent agent of high safety which excels in absorption characteristics and befits sanitary materials can be obtained with high efficiency from the viewpoint of process.

The amount of the cross-linking agent to be used in this invention is generally in the range of from 0.001 to 10 parts by weight, preferably from 0.005 to 8 parts by weight, more preferably from 0.01 to 5 parts by weight, and most preferably from 0.02 to 2 parts by weight, based on 100 parts by weight of the solids of the water-absorbent resin of this invention, through variable with the kind of cross-linking agent to be used. So long as the amount of the cross-linking agent falls within the range specified above, the produced water-absorbent resin exhibits fine absorption characteristics under load. If this amount exceeds 10 parts by weight, the excess will neither bring about any economic advantage nor make any contribution to the accomplishment of the proper effect of cross-linkage but tend to give rise to a residue in spite of the use of the additive of this invention. Conversely, if this amount is less than 0.001 part by weight, then the cross-linking agent will not be amply effective in exalting absorption characteristics under load.

Further, when at least two kinds of the cross-linking agents are used, the use both first and second cross-linking agents mentioned above is preferable, and in such case, the amounts of the first and second cross-linking agents to be used in this invention are variable with the particular kinds of these cross-linking agents to be adopted. Generally, the amount of the first cross-linking agent is in the range of 0.001 to 10 parts by weight and that of the second cross-linking agent in the range of 0.001 to 10 parts by weight, respectively based on 100 parts by weight of the solids of the absorbent resin as the base polymer. The amount of the first cross-linking agent is preferably in the range of 0.01 to 8 parts by weight, more preferably 0.1 to 5 parts by weight and that of the second cross-linking agent is preferably in the range of 0.001 to 1 part by weight, more preferably 0.005 to 0.5 part by weight.

In this invention, it is preferable to use water in mixing the water-absorbent resin and the cross-linking agent. The amount of water thus used in this invention is generally in the range of from 0.5 to 5 parts by weight, preferably from 0.5 to 3 parts by weight, based on 100 parts by weight of the solids of the absorbent resin, though variable with the kind, particle size, and water content of the water-absorbent resin. If the amount of water to be used exceeds 5 parts by weight, the improvement of absorption characteristics under load possibly will not be easily attained and the cross-linking agent will possibly tend to give rise to a residue in spite of the use of the additive of this invention. Conversely, if the amount is less than 0.5 part by weight, the effective improvement of absorption characteristics under load possibly will not be easily attained.

In this invention, the mixture of the absorbent resin with the cross-linking agent may be effected through the medium of a hydrophilic organic solvent. As concrete examples of the hydrophilic organic solvent which is effectively usable herein, lower alcohols such as methyl alcohol, ethyl alcohol, n-propyl alcohol, iso-propyl alcohol, n-butyl alcohol, iso-butyl alcohol, and t-butyl alcohol; ketones such as acetone; ethers such as dioxane, alkoxy(poly)ethylene glycols, and tetrahydrofuran; amides such as N,N-dimethyl formamide; and sulfoxides such as dimethyl sulfoxide may be cited. The amount of the hydrophilic organic solvent to be used in this invention generally is in the range of from 0 to 10 parts by weight, preferably from 0.1 to 5 parts by weight, based on 100 parts by weight of the solids of the water-absorbent resin, though variable with the kind and the particle size of the water-absorbent resin.

In this invention, the mixing of the water-absorbent resin with the cross-linking agent and the additive may be carried out in such a state as has the water-absorbent resin dispersed in an organic solvent like cyclohexane or pentane. The invention is manifested to the fullest possible extent. To be specific, this mixture is preferably accomplished by:

1. A method which comprises preparatorily mixing a cross-linking agent optionally containing water and/or a hydrophilic organic solvent with an additive and subsequently adding the resultant mixture to an absorbent resin by either direct spraying or dropwise incorporation.

2. A method which comprises preparatorily mixing a water-absorbent resin with an additive and subsequently adding to the resultant mixture a cross-linking agent optionally containing water and/or a hydrophilic organic solvent by either spraying or dropwise incorporation.

3. A method which comprises directly adding a cross-linking agent optionally containing water and/or a hydrophilic organic solvent to a water-absorbent resin by either spraying or dropwise incorporation and further mixing an additive therewith.

4. A method which comprises spraying or mixing dropwise the additive optionally with the cross-linking agent containing water and/or hydrophilic organic solvent parallely by two nozzes.

From the standpoint of absorption characteristics and the effective decrease of the amount of a residue of the cross-linking agent, the method 1 mentioned above proves preferable. When the mixture is implemented through the medium of water, it may be carried out in the presence of a water-insoluble finely divided powder or a surfactant.

The device to be used for the mixture must be capable of generating a large mixing force enough to enable the mixture to proceed uniformly. As concrete examples of the mixing device to be effectively usable in this invention, cylindrical mixers, double-wall conical mixers, high-speed stirring type mixers, V-shaped mixers, ribbon type mixers, screw type mixers, fluidized-bed oven rotary disk type mixers, air current type mixers, twin-arms type kneaders, crushing type kneaders, rotary type mixers, and screw type extruders may be cited.

This invention contemplates a procedure which comprises mixing a water-absorbent resin with a cross-linking agent, preferably with both the cross-linking agent and an additive simultaneously by the above-mentioned method 1 and then preferably further heat-treating the resultant mixture depending on the kind of the cross-linking agent thereby cross-linking the surface region of the adhesive resin particles.

When this invention adopts the heat treatment, the temperature of this heat treatment is desired to be in the range of from 80 to 300° C. If the temperature of the heat treatment is lower than 80° C., the heat treatment will consume time so much as to induce degradation of productivity, obstruct uniform progress of cross-linkage, possibly prevent production of a resin of high absorption characteristics under load, and suffer the cross-linking agent to give rise to a residue. The temperature of the heat treatment is preferably in the range of from 100 to 230° C., more preferably from 160 to 220° C., though variable with the kind of cross-linking agent to be used.

The heat treatment can be performed by the use of a standard drier or a standard heating furnace. As typical examples of the heating device effectively usable herein, groove type combination mixers and driers, rotary driers, dick driers, fluidized-bed type driers, air current type driers, and infrared driers may be cited.

The water-absorbent agent which is obtained by the method of production of this invention described above is a product of the addition of from 0.005 to 8% by weight of an epoxy compound to a water-absorbent resin containing carboxyl group. It is water-absorption agent which exhibits an absorption capacity wihtout load of not less than 45 (g/g) and an absorption capacity under load of 20 g/cm$^2$ of not less than 30 (ml/g), preferably not less than 35 (ml/g), and possesses a residue amount of an epoxy compound concentration of not more than 2 ppm, preferably 0 ppm. The water-absorbent agent of this invention preferably contains from 0.01 to 5% by weight of a saturated organic acid, preferably a hydroxy group-containing saturated organic acid in respect of safety and absorption properties.

Heretofore, when the cross-linking agent such as an epoxy compound is used for surface cross-linking, it has inevitably entailed the occurrence of a residue of the order of from some tens to 1,000 ppm. The water-absorbent agent which is obtained by this invention exhibits outstanding absorption characteristics both without load and under load and reveals a notable decrease of the amount of a residue of a cross-linking agent of high reactivity on the resin surface. The cause for these advantages of this invention has not been clearly defined. They may be logically explained by a postulate that when the water-absorbent resin is mixed the cross-linking agent with the additive of this invention, the additive discharges the role of optimizing the distribution of the cross-linking agent in the surface region of the water-absorbent resin particles and, at the same time, accelerating and uniformizing the reaction between the absorbent resin and the cross-linking agent and consequently notably decreasing the amount of a residue of the cross-linking agent and enabling the cross-linkage of uniform density gradient to be formed in the surface region of the water-absorbent resin particles. When the water-absorbent resin is produced in the form of irregular broken particles as mentioned previously, it enjoys such advantages as high safety, thorough diffusion of liquid, and perfect absence of migration or exfoliation of resin particles from pulp in addition to the excellent absorption characteristics mentioned above. Thus, this absorbent resin is particularly adapted for absorbent products such as disposable diaper and sanitary materials.

This invention also provides a novel water-absorbent composition which comprises a polyamino acid (salt) and a carboxyl group-containing water-absorbent resin. As the polyamino acid(salt) for use in this water-absorbent composition, the polyamino acids previously cited as additives for the surface cross-linkage of the absorbent resin mentioned above are available. Preferably, in addition to such poly(monoaminodicarboxylic acids) as polyaspartic acid and polyglutamic acid which are advantageously used for the surface cross-linkage, polylysine and polyarginine and more desirably such poly(diaminomonocarboxylic acids) and salts thereof as polylysine are used favorably in the composition of this invention.

The water-absorbent composition of this invention is essentially composed of the absorbent resin mentioned above and the polyamino acid (salt). Preferably, the ratio of the polyamino acid (salt) is in the range of from 0.005 to 30 parts by weight, preferably from 0.005 to 8 parts by weight, most preferably from 0.01 to 5 parts by weight, to 100 parts by weight of the water-absorbent resin. If the amount of the polyamino acid (salt) is smaller than the lower limit of the range mentioned above, the effect of this invention will not be produced. Conversely, it is larger than the upper limit of the range, the excess will not bring about a proportional increase to the effect but will possibly degrade the absorption quality.

The water-absorbent composition of this invention is favorably obtained by a method which essentially uses the polyamino acid during the surface cross-linkage of the water-absorbent resin described above. In this case, the water-absorbent composition containing the polyamino acid (salt) is formed. The acid type polyamino acid is ideally used for decreasing the amount of a residue of the cross-linking agent. For the purpose of improving the absorption of blood which constitutes another object of this invention, substantially the same effect can be attained with the absorbent composition incorporating therein an amino polyacid salt.

For the production of the water-absorbent composition of this invention, therefore, a method which consists in effecting the addition of the polyamino acid (salt) in the process of the formation of the water-absorbent resin may be adopted besides the method which resorts to the surface cross-linkage. Specifically, the polyamino acid (salt) may be added to the aqueous monomer solution prior to polymerization or to the reaction solution during or after polymerization. Otherwise, a method which resides in causing the polyamino acid (salt) to be added to the water-absorbent resin after the resin has been formed may be adopted. For the addition of the polyamino acid (salt) to the water-absorbent resin in the dry state, the so-called dry blend method which comprises mechanically mixing the two components both in a powdered state or the method which effects the mixture by adding either or both of the two components in the form of an aqueous dispersion or aqueous solution. Among other methods cited above, the method which resides in adding the polyamino acid (salt) in the form of an aqueous liquid or a dispersion, preferably the aqueous liquid to the water-absorbent resin in a dry state proves particularly preferable in respect that the produced water-absorbent composition excels in various properties. In this case, water alone or a mixture of water with a hydrophilic organic solvent can be used as the aqueous liquid.

The amount of the aqueous liquid to be used is in the range of from 0.1 to 50 parts by weight, preferably from 1 to 30 parts by weight, based on 100 parts by weight of the solid of the water-absorbent resin. As typical examples of the hydrophilic organic solvent to be used in the mixture mentioned above, lower alcohols such as methyl alcohol, ethyl alcohol, n-propyl alcohol, iso-propyl alcohol, n-butyl alcohol, iso-butyl alcohol, and t-butyl alcohol; ketones such as acetone; ethers such as dioxane, alkoxy(poly)ethylene glycol and tetrahydrofuran; amides such as N,N-dimethyl formamide; and sulfoxides such as dimethyl sulfoxide may be cited.

Further in this invention, the water-absorbent composition having the polyamino acid (salt) added in the form of an aqueous liquid to the water-absorbent resin is subjected to a heat treatment when necessary. The temperature of this heat treatment is generally in the range of from 50° to 300° C., preferably 100° to 230° C., though variable with the amount of the aqueous liquid to be added. The heat treatment is desired to be effected under conditions such that the water-absorbent composition of this invention may be obtained in a substantially dried state.

When the water-absorbent resin is mixed with the polyamino acid in the aqueous liquid as described above, particularly by causing a cross-linking agent capable of reacting with the carboxyl group to be preparatorily contained in the aqueous liquid and as above-mentioned heat-treating the resultant mixture thereby introducing a cross-linked structure in the surface region of the water-absorbent resin, the water-absorbent composition to be produced by this invention is enabled to acquire an ability to aspirate physiological saline solution and blood and excel particularly in absorption capacity under load.

The water-absorbent composition of this invention obtained as described above is a novel water-absorbent composition which exhibits outstanding absorption characteristics to such body liquids as urine, blood, and excretion, manifests fine gel stability, high flowability (anti-blocking property) after absorbing moisture, static charge, and the rustproofing effect.

This invention has brought to light a novel water-absorbent composition which exhibits an excellent suction power to physiological saline solution and bovine blood. Heretofore, the fact that the water-absorbent agent having an aspirating capacity of not less than 14 g/g of artificial urine, when used in a disposable diaper, is capable of repressing leakage (JP-A-63-21,902) and the absorbent material which exhibits an excellent absorption capacity to blood (JP-A-06-25,543) have been known to the art. These known techniques do not necessarily generate a fully satisfactory aspirating capacity on such highly viscous liquids as blood, menstrual fluid, and loose feces. The present invention offers a water-absorbent composition which has overcome the heretofore insoluble problems. It has been ascertained by this invention that for sanitary napkins and disposable diapers using a water-absorbent composition at high concentrations (the absorbent structures containing the absorption composition at concentrations of not less than 50% by weight), the balance among the absorption capacity without load and the suction power exhibited to physiological saline solution and the suction power exhibited to bovine blood, i.e. the characteristic feature presented by the water-absorbent composition of this invention, constitutes an important requirement.

Thus, this invention provides a water-absorbent composition which exhibits an absorption capacity without load of at least 25 g/g to physiological saline solution and a suction power of not less than 14 g/g to physiological saline solution and a suction power of at least 7 g/g to bovine blood and also provides a water-absorbent structure and a water-absorbent article both incorporating therein the absorbent composition or the absorbent agent mentioned above.

The suction power of the water-absorbent composition exhibited to physiological saline solution and that exhibited to bovine blood constitute essential factors for the acquisition of such a water-absorbent article as disposable diaper or sanitary napkin or similar sanitary material which quickly absorbs urine or blood diffused in a hydrophilic fibrous material supporting the water-absorbent composition, retains the diffusing property of the hydrophilic fibrous material stably to withstand the effect of aging, avoids inflicting an offensive sensation to the skin, and represses the amount of urine or blood suffered to flow back. It has been ascertained particularly that the ratio of the absorbent composition incorporated in the water-absorbent structure is allowed to be notably increased (to 50% by weight or even higher) when the suction power exhibited to bovine blood exceeds 7 g/g. The cause for this feature is not clear. The feature may be logically explained, however, by a supposition that the proportion of blocks generated between particles owing to the high concentration of the water-absorbent composition in the water-absorbent structure is increased when the water-absorbent structure is used on such a viscous liquid as blood. Thus, it is inferred that the differences brought out in absorption characteristics exhibited to bovine blood play an important role.

The absorption capacity without load exhibited to physiological saline solution constitutes an important factor in respect that it governs the absorption capacity of the water-absorbent article.

This absorption capacity without load is such that the suction power and the absorption ratio under load are decreased in proportion as the absorption capacity without load is increased. Thus, the absorption capacity without load has a relation of antinomy relative to the suction capacity and the absorption capacity under load. By causing the water-absorbent composition of this invention which have the absorption capacity without load, the suction power, and the absorption capacity under load controlled within the specific ranges to be combined at a specific mixing ratio with the hydrophilic fibers and the water absorbent, the absorbent structure and the water-absorbent article of this invention which possess the heretofore unattainable absorption characteristics can be obtained.

The hydrophilic fibers for use in the absorbent structure of this invention are desired to be in the form of an airlaid batt of ground wood pulp. The structure of this airlaid batt is well known in the field of manufacture of disposable diapers as disclosed in U.S. Pat. No. 4,610,678, for example. As typical examples of the hydrophilic fibers which are effectively usable for this invention, cotton linters, such cross-linked cellulose fibers as are disclosed in EP-A-0429112 and EP-A-0427316, rayon fibers, cotton fibers, wool fibers, acetate fibers and vinylon fibers may be cited besides the ground pulp.

The water-absorbent structure of this invention is composed of from 10 to 95 parts by weight of a water-absorbent composition or water-absorbent agent and from 90 to 5 parts by weight of absorbent fibers, preferably from 50 to 95% by weight of the water-absorbent composition and 50 to 5% by weight of the hydrophilic fibers. The composition and the fibers are combined to form a matrix as intermixed or dispersed on a fibrous sheet. Several methods including the method currently adopted for the manufacture of disposable diapers on the market are available for the formation of the water-absorbent structure. Methods proper for the formation of the absorbent structure are disclosed in U.S. Pat. No. 4,578,068, U.S. Pat. No. 4,666,975, U.S. Pat. No. 4,673,402, U.S. Pat. No. 4,685,915, U.S. Pat. No. 4,765,780, U.S. Pat. No. 5,047,023, and U.S. Pat. No. 5,156,902, for example. The water-absorbent structure which is obtained as described above is preferably compression molded until the density thereof reaches a level in the range of from 0.06 to 0.5 g/cc. In this invention, therefore, the density is preferable to fall in this range because the absorbent structure which contains the water-absorbent composition or the water-absorbent agent at a relatively high concentration has a relative small thickness and manifests the absorbing power efficiently. If the density exceeds the upper limit of this range, the water-absorbent structure will be unduly hard. Conversely, if the density falls below the lower limit of the range, the water-absorbent structure will be deficient in the efficiency of absorption. The water-absorption structure of this invention is preferable to have a basis weight in the range of from 0.01 to 0.20 g/square centimeter. If the basis weight is smaller than the lower limit of the range, the water-absorbent structure will be deficient in strength. If it is larger than the upper limit of the range, the water-absorbent structure possibly will be too hard to be favorably adapted for absorbent articles. The water-absorbent structure of this invention, therefore, is allowed to have an average thickness less than 40 mm, preferably less than 10 mm, and more preferably less than 5 mm.

In the present invention, the water-absorbent structure which comprises the water-absorbent composition or the water-absorbent agent and the hydrophilic fibers is allowed to contain therein up to 40 parts by weight of thermoplastic fibers based on 100 parts by weight of the hydrophilic fibers for the purpose of enabling the water-absorbent structure to retain the shape thereof during the absorption of water. As typical examples of the thermoplastic fibers which are effectively used for the purpose just mentioned, polyethylene, polypropylene, and polyester fibers, and bicomponent fibrous copolymers of polyester and polyamides and complex fibers thereof may be cited.

The water-absorbent structure of this invention which is obtained as described above is nipped fast between a facing member pervious to liquid and a backing member impervious to liquid to produce a water-absorbent article of this invention.

The water-absorbent article of this invention may be provided with numerous members such as a diffused layer, an elastic leg part member, an elastic waist part member, and tapes which are well known in the technical field to which this invention pertains.

The water-absorbent article of this invention can be adapted for various products such as disposable diapers, athlet's pants, sanitary napkins, surgical pads, clothing for patients of incontinence, and sheets for pets which are required to absorb large volumes of liquid.

The water-absorbent agent, the water-absorbent composition, or the water-absorbent structure which is obtained by this invention may be endowed with a new function by addition of such additives as deodorant, perfume, inorganic powder, foaming agent, pigment, dye, hydrophilic short fibers, plasticizer, binder, fertilizer, oxidizing agent, reducing agent, water, and salts or may be granulated. Typical examples of these additives are cited in U.S. Pat. No. 4,179,367, U.S. Pat. No. 4,190,563, U.S. Pat. No. 4,500,670, U.S. Pat. No. 4,693,713, U.S. Pat. No. 4,812,486, U.S. Pat. No. 4,863,989, U.S. Pat. No. 4,929,717, U.S. Pat. No. 4,959,060, U.S. Pat. No. 4,972,019, U.S. Pat. No. 5,078,992, and U.S. Pat. No. 5,229,488, EP-A-0009977 and EP-A-0493011. Typical examples of the method of granulation are cited in U.S. Pat. No. 4,734,478 and EP-A-0450922 and EP-A-0480031, for example.

Now, the present invention will be described specifically below with reference to working examples. It should be noted, however, that these examples are not meant to define the scope of the present invention. All "parts" in examples are by weight unless they are specifically noticed.

Various properties of the water-absorbent agents indicated in the examples were determined by the following methods.

(a) Absorption Capacity to Physiological Saline Without Load

A teabag pouch of non-woven fabric (40 mm×150 mm) having 0.2 g of a sample water-absorbent or water-absorbent composition uniformly contained therein was immersed in an aqueous solution containing excess amount of 0.9% by weight of sodium chloride (physiological saline solution). After 60 minutes' standing in the saline solution, the teabag pouch containing a swelled gel was pulled out over a period of 5 seconds from the saline solution, left draining for 10 seconds on 24 superposed sheets of toilet papers (57 mm×50 mm, 19 g/m$^2$ per 1 sheet), and then weighed (W1). The same procedure was repeated by way of a blank test using no sample to find the blank weight of the teabag pouch (W0). The absorption capacity without load was calculated in accordance with the following formula 1.

Absorption capacity without load to physiological saline (g/g)=[Weight, $W_1$(g), after absorption– Blank weight, $W_0$(g)]/(Weight of absorbent resin agent (or composition)(g)) (1)

(b) Absorption Capacity Under Load

The absorption capacity under load was determined by the use of the same device as illustrated in FIGURE. With an upper mouth 2 of a buret 1 closed with a stopper 3, a measuring base 4 and an air inlet 5 were set at an equal level. A filter paper 7 was mounted on a glass filter 6 of a diameter of 70 mm located in the central part of the measuring base 4. A non-woven fabric 8 was fixed at the lower end part of a supporting cylinder 10 having a diameter of 55 mm. On the non-woven fabric 8, 0.76 g of a sample water-absorbent agent was uniformly spread and a load 9 of 20 g/cm$^2$ was placed. This set of non-woven fabric, water-absorbent agent, and load as held on the supporting cylinder 10 was mounted on the filter paper 7 overlying the glass filter 6. The amount (A ml) of the aqueous solution of 0.9% by weight of sodium chloride (physiological saline solution) absorbed over a period of 30 minutes was measured. The absorption capacity (ml/g) under load was calculated in accordance with the following formula 2.

Absorption capacity under load (ml/g)=$A$(ml)/0.76(g) (2)

(c) Amount of Residue of Surface Cross-Linking Agent (in the Case of an Epoxy Compound)

In a beaker having an inner volume of 100 ml, 2.0 g of a sample water-absorbent agent was placed and 2 ml of a composed solution of methanol/water=2/1% by weight was added thereto and the resultant mixture was left standing for one hour, with the beaker kept closed with a lid. The sample remaining in the beaker was mixed with 5 ml of methanol and the resultant mixture was filtered. In an eggplant flask having an inner volume of 50 ml, 1.0 g of the filtrate was placed and combined with 0.05 ml of an aqueous solution of 12 wt % of nicotine amide. The flask was fitted with an air cooling tube and heated in a water bath for 30 minutes. The reaction solution was passed through a filter paper and the filtrate was assayed by high-performance liquid chromatography.

Separately, the same procedure was repeated by way of a blank test using a known amount of cross-linking agent and omitting the use of a water-absorbent agent to obtain a calibration curve. With this calibration curve as an external standard and in due consideration of the ratio of dilution of the filtrate, the amount of residue of surface cross-linking agent on (ppm) in the sample was determined.

(d) Suction Power to Physiological Saline Solution

About 1 g of a sample water-absorption agent (or composition) was placed on 16 superposed sheets of toilet paper (19 g/m², 55 mm×75 mm per 1 sheet) kept immersed in 20 ml of the physiological saline solution held in a petri dish 95 mm in inside diameter and then allowed to aspirate the saline solution for 10 minutes. Then the swelled gel consequently formed was collected and weighed. The capacity of the sample water-absorbent agent or composition for absorption of the physiological saline solution (g/g) was calculated by dividing the weight of the swelled gel by the original weight of the water-absorbent agent (or composition).

(e) Suction Power to Bovine Blood

The suction power to bovine blood (g/g) was determined by faithfully repeating the procedure used for the determination of the suction power to physiological saline solution while using bovine blood [bovine blood liquid prepared by reconstituting a freeze dried product of Wako Pure Chemical Industries, Ltd. marketed under "Wako Code Number 029-07071"] in the place of physiological saline solution.

(f) Flowability (Anti Blocking Property) After Absorbing Moisture

This property was rated by causing an aluminum cup (50 mm in diameter on the bottom side and 23 mm in height) containing 2 g of a sample water-absorbent composition to stand at rest for 1.5 hours in a thermo-hygrostat regulated at 25° C. and 50% RH and, after the standing, removing the aluminum cup and tilting it at an angle of 30° and visually examining the condition of flow of the absorbent composition in the aluminum cup.

(g) Rustproofing Effect and Gel Stability

This property was determined by placing 1 g of a sample water-absorbent composition in 25 cc of physiological saline solution held in a lidded container of polypropylene measuring 55 mm in diameter and 70 mm in height thereby allowing the sample to swell with the saline solution, thoroughly immersing an iron clip in the resultant swelled gel, and allowing the iron clip to stand at rest therein for three days at normal room temperature and, at the end of the standing, visually examining the gel to find whether or not the iron clip produced rust in the gel. The visual observation of the gel was concurrently utilized for rating the stability of the gel.

(h) Ability to Prevent Static Charge

This property was determined by placing 10 g of a sample water-absorbent composition in a polyethylene bag fitted with a slide fastener (140 mm×100 mm×0.04 mm, produced by Seisan Nippon K.K. and marketed under trademark designation of "Unipack E-4"), closing the bag, vigorously shaking the bag vertically for one minute, and visually examining the bag to rate the extent of adhesion of the water-absorbent composition to the inner walls of the bag.

REFERENTIAL EXAMPLE 1

In 5500 g an aqueous solution of sodium acrylate having a ratio of neutralization of 75 mol % (monomer concentration 33%), 1.58 g of N,N'-methylene-bis-acrylamide as a inner cross-linking agent was dissolved. The resultant solution was deaerated by bubbling nitrogen gas therethrough for 30 minutes and then supplied into a reaction vessel constructed by lidding a jacketed twin arm type kneader of stainless steel having an inner volume of 10 liters and provided with two sigma vanes. The reaction vessel was further subjected to displacement of the entrapped air with nitrogen gas, with the monomer kept at 30° C. When 2.4 g of ammonium persulfate and 0.12 g of 1-ascorbic acid were added to the reaction system with the vanes kept in rotation meanwhile, the monomer therein began to polymerize 1 minute thereafter. After the further elapse of 16 minutes thereafter, the inner temperature of the reaction system reached 83° C. and the cross-linked hydrogel polymer produced meanwhile was finely divided into particles about 5 mm in diameter. Then, the stirring of the contents of the reaction vessel was continued. The cross-linked hydrogel polymer was removed from the reaction vessel after the elapse of 60 minutes following the start of the polymerization.

The finely divided particles of the cross-linked hydrogel polymer thus obtained were spread on a metal gauze of ASTM 50-mesh and dried with hot air at 150° C. for 90 minutes. The dried particles were pulverized with a shaking mill and further classified with an ASTM 20-mesh sieve to obtain an irregular broken water-absorbent resin (A) having average diameter of 360 μm and containing resin particles of diameters of less than 150 μm at a proportion of 5% by weight and having a water content of 6% by weight.

REFERENTIAL EXAMPLE 2

In 5500 g of an aqueous solution of sodium acrylate having a ratio of neutralization of 75 mol % (monomer concentration of 33%), 4.4 g of polyethylene glycol diacrylate as the inner cross-linking agent was dissolved. The resultant solution was deaerated with nitrogen gas and then combined with 2.4 g of sodium persulfate and 0.12 g of 1-ascorbic acid to set the monomer to polymerizing. At the time that the polymerization was completed, the cross-linked hydrogel polymer produced in the meanwhile was finely divided and dried in a hot air drier at 150° C. The dried particles of the polymer consequently obtained were pulverized with a roll granulator and classified with an ASTM 20-mesh sieve to obtain an irregular broken water-absorbent resin (B) having an average particle diameter of 400 μm and containing resin particles of diameters of less than 150 μm at a proportion of 5% by weight and having a water content of 6% by weight.

REFERENTIAL EXAMPLE 3

In 5500 g of an aqueous solution of sodium acrylate having a ratio of neutralization of 75 mol % (monomer concentration of 38%), 7 g of trimethylol propane triacrylate as the inner cross-linking agent was dissolved. The resultant solution was deaerated with nitrogen gas and then combined with 2.3 g of potassium persulfate and 0.11 g of 1-ascorbic acid to set the monomer to polymerizing. At the time that the polymerization was completed, the cross-linked hydrogel polymer produced in the meanwhile was finely divided and dried in a hot air drier at 150° C. The dried particles of the polymer consequently obtained were pulverized with a roll granulator and classified with an ASTM 20-mesh sieve to obtain an irregular broken water-absorbent resin (C) having an average particle diameter of 380 μm and containing resin particles of diameters of less than 150 μm at a proportion of 5% by weight and having a water content of 5% by weight.

REFERENTIAL EXAMPLE 4

An irregular broken water-absorbent resin (D) was obtained by mixing 100 parts of the water-absorbent resin (B) obtained in Referential Example 2 with a liquid composed of 0.5 part of glycerol as a first cross-linking agent, 0.05 part of ethylene glycol diglycidyl ether as a second cross-linking agent, 3 parts of water, and 0.75 part of isopropyl alcohol and heat-treating the resultant mixture at 200° C. for 35 minutes.

EXAMPLE 1

A water-absorbent agent (1) was obtained by mixing 100 parts of the water-absorbent resin (A) obtained in Referential Example 1 with a liquid composed of 0.05 part of ethylene glycol diglycidyl ether as a cross-linking agent, 0.5 part of lactic acid (pKa=3.66) as an additive, and 3 parts of water and heat-treating the resultant mixture at 120° C. for 40 minutes. The water-absorbent agent (1) was tested for properties. The results of the test are shown in Table 1.

EXAMPLE 2

A water-absorbent agent (2) was obtained by mixing 100 parts of the water-absorbent resin (A) obtained in Referential Example 1 with a liquid composed of 0.5 part of glycerol as a first cross-linking agent, 0.05 part of ethylene glycol diglycidyl ether as a second cross-linking agent, 0.5 part of citric acid (pKa=2.87) as an additive, 3 part of water, and 1 part of isopropyl alcohol and heat-treating the resultant mixture at 200° C. for 40 minutes. The water-absorbent agent (2) was tested for properties. The results of the test are shown in Table 1.

EXAMPLE 3

A water-absorbent agent (3) was obtained by repeating the procedure of Example 2 while using 0.2 part of phosphoric acid (pKa=2.15) instead as an additive and tested for properties. The results of the test are shown in Table 1.

EXAMPLE 4

A water-absorbent agent (4) was obtained by mixing 100 parts of the water-absorbent resin (A) obtained in Referential Example 1 with a liquid composed of 1 part of ethylene carbonate as a first cross-linking agent, 0.05 part of glycerol polyglycidyl ether as a second cross-linking agent, 0.02 part of succinic acid (pKa=4.00) as an additive, 2 parts of water, and 3 parts of isopropyl alcohol and heat-treating the resultant mixture at 190° C. for 60 minutes. The water-absorbent agent (4) was tested for properties. The results of the test are shown in Table 1.

EXAMPLE 5

A water-absorbent agent (5) was obtained by mixing 100 parts of the water-absorbent resin (B) obtained in Referential Example 2 with a liquid composed 0.5 part of glycerol as a first cross linking agent, 0.05 part of ethylene glycol diglycidyl ether as a second cross-linking agent, 3 parts of water, 0.75 part of isopropyl alcohol, and 0.5 part of polyaspartic acid (molecular weight 10000) as an additive and heat-treating the resultant mixture at 200° C. for 33 minutes. The water-absorbent agent (5) was also an absorbent composition (1) of this invention containing 0.5 part of polyaspartic acid (sodium salt).

EXAMPLE 6 AND EXAMPLE 7

The water-absorbent agents (6) and (7) were obtained by mixing 100 parts of the water-absorbent resin (D) obtained in Referential Example 4 severally with an aqueous solution (10 parts of water) of 5 parts of aspartic acid (molecular weight 50000) and an aqueous solution of 1 part of polyglutamate (molecular weight 100000) as an additive and drying the resultant mixtures at 0.120° C. These water-absorbent agents (6) and (7) obtained by adding the additive after adding a surface cross-linking agent were also water-absorbent compositions (2) and (3) of this invention respectively containing polyaspartic acid (sodium salt) and polyglutamic acid (sodium salt).

EXAMPLE 8

A water absorbent composition (4) of this invention was obtained by mixing 100 parts of the water-absorbent resin (3) obtained in Referential Example 3 with an aqueous liquid composed of 1 part of polysodium aspartate (molecular weight 10000) and 5 parts of water.

EXAMPLE 9

A water-absorbent resin composition (5) containing a polylysine salt was obtained by dry blending 100 parts of the absorbent resin (4) obtained in Referential Example 4 with 10 parts of polylysine hydrochloride (molecular weight of 2000).

EXAMPLE 10

A water-absorbent composition (6) containing polysodium aspartate was obtained by repeating the procedure of Referential Example 3 while having 104.5 g of polysodium aspartate (molecular weight 10000) additionally dissolved in the aqueous sodium acrylate solution (5% as solids based on the monomer) thereby having the polysodium aspartate additionally incorporated in the monomer being polymerized, then continuing the polymerization, and subjecting the resultant cross-linked hydrogel polymer to fine division, drying, and pulverization. The water-absorbent composition (6) thus obtained, while showing substantially the same absorption capacity as the water absorbent resin (C) having used no polysodium aspartate in the polymerization, excelled the water-absorbent resin (3) in the flowability after absorbing moisture, the rustproofing effect, the gel stability, and the ability to resist static charging. By the pH titration, this composition (6) was found to have a water-soluble component of less than about 4% by weight compared to the water-absobent resin (C).

Control 1

A water-absorbent agent (1) for comparison was obtained by following the procedure of Example 1 while omitting the use of lactic acid as an additive. The water absorbent agent (1) for comparison was tested for properties. The results of this test are shown in Table 1.

Control 2

A water-absorbent agent (2) for comparison was obtained by following the procedure of Example 1 while using 0.5 part of sodium lactate in the place of lactic acid as an additive. The water-absorbent agent (2) for comparison was tested for properties. The results of this test are shown in Table 1.

Control 3

A water-absorbent agent (3) for comparison was obtained by following the procedure of Example 2 while using 0.5 part of sodium citrate in the place of citric acid as an additive. The water-absorbent agent (3) for comparison was tested for properties. The results of this test are shown in Table 1.

Control 4

A water-absorbent agent (4) for comparison was obtained by following the procedure of Example 2 while using 0.5 part of monosodium succinate in the place of citric acid as an additive. The water-absorbent agent (4) for comparison was tested for properties. The results of this test are shown in Table 1.

Control 5

The water-absorbent resin (D) obtained in Referntioal Example 4 was used in its unmodified form as a water-absorbent agent (5) for comparison.

EXAMPLE 11

The water-absorbent compositions (1) through (5) conforming to this invention and the water-absorbent resins (B) through (D) as water-absorbent compositions (1) through (3) for comparison were tested for absorption capacity without load to physiological saline solution, suction power to physiological saline solution, suction power to bovine blood, flowability after absorbing moisture, rustproofing effect, and ability to resist static charging. The results of the test are shown in Table 2. It is clearly noted from the test results that the water-absorbent composition of this invention excels also in the flowability after absorbing moisture, the rustproofing effect, and the ability to resist static charging.

EXAMPLE 12

A water-absorbent structure (1) of this invention having a density of 0.15 g/cc and a basis weight of 0.05 g/square centimeter was obtained by dry mixing 100 parts of the water-absorbent composition (4) of this invention with 100 parts of ground pulp, pneumatically molding the resultant mixture in the form of sheet, and compressing the sheet.

EXAMPLE 13

Water-absorbent structures (2) through (5) of this invention and water-absorbent structures (1) through (3) for comparison having a density in the approximate range of from 0.13 to 0.17 g/co and a basis weight in the approximate range of from 0.047 to 0.053 g/cm$^2$ were obtained by following the procedure of Example 12 while using the absorbent compositions (1) through (3) and (5) and the absorbent compositions (1) through (3) for comparison in the place of the water-absorbent composition (4).

EXAMPLE 14

Water-absorbent structures of 5 cm in diameter were each punched out of the water-absorbent structures (1) through (5) obtained in Examples 12 and 13 and the water-absorbent structures (1) through (3) to be used as test pieces. When 10 cc of bovine blood was dropped onto the test pieces, the water-absorbent structures of this invention showed better results in terms of the absorption speed than the water-absorbent structures for comparison. It is clearly noted from the test results that the water-absorbent structures containing the water-absorbent compositions of this invention exhibit excellent suction power to bovine blood. Thus, the water-absorbent structures of this invention promise to provide water-absorbent articles of heretofore unattainable quality.

EXAMPLE 15

A water-absorbent structure (6) of this invention having a density of 0.18 g/co and a basis weight of 0.05 g/cm$^2$ was obtained by dry mixing 75 parts of the water-absorbent composition (4) of this invention with 25 parts of ground pulp and 10 parts of thermoplastic fibers (ES filters 1.5 d, 10 mm, produced by Chisso Corporation), pneumatically molding the resultant mixture in the form of sheet, and thermally compressing the sheet.

EXAMPLE 16

Water-absorbent structures (7) and (8) of this invention and water-absorbent structures (4) through (6) for comparison substantially equalling in density and basis weight were obtained by following the procedure of Example 15 while using, in the place of the water-absorbent composition (4) of this invention of Example 15, water-absorbent compositions differing in the absorption capacity without load to physiological saline solution, the suction power to physiological saline solution, and the suction power to bovine blood.

EXAMPLE 17

Water-absorbent articles (1) through (3) of this invention and water-absorbent articles (1) through (3) for comparison were fabricated by the following procedure using the water-absorbent structures (6) through (8) of this invention and the water-absorbent structures (4) through (6) for comparison obtained in Examples 15 and 16. A disposable diaper comprising a top sheet of polypropylene pervious to liquid, two sheets of tissue paper, a sample water-absorbent structure (weight about 24 g) cut in a size of 12 cm×40 cm, a back sheet of polyethylene impervious to liquid including leg gathers and a waist gather, and two tape fasteners was manually assembled by joining the individual component parts. The total weight of the diaper was about 45 g.

EXAMPLE 18

Ten babies were made to wear randomly 30 pieces each of the water-absorbent articles (1) through (3) of this invention and the water-absorbent articles (1) through (3) for comparison obtained in Example 17. The samples thus used on the babies were recovered and visually examined to determine the ratio of leakage. The results are shown in Table 2. It is clearly noted from the test results that the water-absorbent structures containing water-absorbent compositions at a relatively high concentration showed no satisfactory quality when the suction power to bovine blood were less than 7 g/g even when the suction power to physiological saline solution were not less than 14 g/g. Thus, this invention provides means to select water-absorbent compositions which are effective in improving the qualities of water-absorbent articles containing water-absorbent compositions at a high concentration.

EXAMPLE 19

A water-absorbent structure (9) of this invention and a water-absorbent structure (7) for comparison substantially equalling in density and basis weight were obtained by following the procedure of Example 15 while using the absorbent agent (2) and the water-absorbent agent (1) for comparison respectively obtained in Example 2 and Control 1 from the same water-absorbent resin (A) in the place of the water-absorbent composition of this invention.

Disposable diapers were assembled with the water-absorbent structure (9) and the water-absorbent structure (7) for comparison by following the procedure of Example 17, to obtain a water-absorbent article (4) of this invention and a water-absorbent article (4) for comparison. The samples of the water-absorbent article (4) and the water-absorbent article (4) for comparison were tried on babies in the same manner as in Example 18. In the test, the water-absorbent article (4) using the water-absorbent agent (2) obtained by the method of production of this invention was found to show a ratio of leakage of 3.3%, whereas the water-absorbent article (4) for comparison using the water-absorbent agent (1) for comparison was found to show a ratio of leakage of 13.3%. Thus, the water-absorbent agent obtained by the method of production of this invention shows no detectable residue of a cross-linking agent used therein and exhibits a high absorption capacity under load as without load and, therefore, is ideally adapted for water-absorbent structures and water-absorbent articles such as disposable diapers.

TABLE 1

|  | Absorption capacity to phyological saline without load (g/g) | Absorption capacity under load (ml/g) | Amount of residue of surface cross-linking agent on surface (ppm) | Suction power to physiological saline solution (g/g) |
| --- | --- | --- | --- | --- |
| water-absorbent agent (1) | 51 | 31 | ND | 17.3 |
| water-absorbent agent (2) | 53 | 36 | ND | 17.5 |
| water-absorbent agent (3) | 52 | 35 | 2 | 17.0 |
| water-absorbent agent (4) | 52 | 35 | ND | 17.2 |
| water-absorbent agent (5) | 52 | 33 | 2 | 17.4 |
| water-absorbent agent (6) | 51 | 29 | 5 | 17.0 |
| water-absorbent agent (7) | 50 | 28 | 5 | 17.3 |
| water-absorbent agent (1) for comparison | 53 | 29 | 30 | 16.9 |
| water-absorbent agent (2) for comparison | 52 | 30 | 12 | 17.0 |
| water-absorbent agent (3) for comparison | 52 | 34 | 12 | 17.1 |
| water-absorbent agent (4) for comparison | 53 | 33 | 9 | 16.9 |
| water-absorbent agent (5) for comparison | 51 | 29 | 15 | 17.5 |

ND: no detectable

TABLE 2

|  | Absorption capacity to physiological saline solution without load (g/g) | Suction power to physiological saline solution (g/g) | Suction power to bovine blood (g/g) | Flowability after absorbing moisture | Ability to Rustproofing effect | Gel Stability | resist static charging |
| --- | --- | --- | --- | --- | --- | --- | --- |
| water-absorbent composition (1) | 52 | 17.4 | 10.3 | good | no rust | no detrioration | almost, no adhesion |
| water-absorbent composition (2) | 50 | 17.0 | 7.2 | good | no rust | no detrioration | almost, no adhesion |
| water-absorbent composition (3) | 51 | 17.3 | 6.3 | good | no rust | no detrioration | almost, no adhesion |
| water-absorbent composition (4) | 40 | 15.3 | 8.4 | good | no rust | no detrioration | almost, no adhesion |
| water-absorbent composition (5) | 49 | 16.8 | 6.9 | good | no rust | no detrioration | almost, no adhesion |
| water-absorbent composition (1) for comparison | 58 | 9.5 | 1.8 | aggregation | rust | detrioration | large adhesion |
| water-absorbent composition (2) for comparison | 40 | 15.2 | 3.5 | aggregation | rust | little detrioration | large adhesion |
| water-absorbent composition (3) for comparison | 51 | 17.5 | 5.2 | little aggregation | rust | little detrioration | large adhesion |

TABLE 3

|  | Physical properties of water-absorbent composition | | | Physical property of absorbent article |
| --- | --- | --- | --- | --- |
|  | Absorption capacity under load to physiological saline solution (g/g) | Suction power to physiological saline solution (g/g) | Suction power to bovine blood (g/g) | Ratio of leakage (%) |
| Absorbent article (1) | 40 | 15.3 | 8.4 | 6.7 |
| Absorbent article (2) | 52 | 17.4 | 10.3 | 6.7 |
| Absorbent article (3) | 50 | 17.0 | 7.2 | 10.0 |
| Absorbent article (1) for comparison | 40 | 16.2 | 2.3 | 20.0 |
| Absorbent article (2) for comparison | 42 | 14.9 | 2.1 | 13.3 |
| Absorbent article (3) for comparison | 58 | 16.8 | 3.3 | 16.7 |

(1) The water-absorbent polymer extracted from commercially available disposable diaper (produced by Shin-Oji Seishi K.K. and marketed under trademark designation of "Doremi") used.
(2) A commercially available water-absorbent polymer (produced by Hoechst Celanese K.K. and marketed under product code of "IM3900") was used.
(3) The water-absorbent polymer extracted from commercially available disposable diaper (produced by Dai-Oh Seishi K.K. and marketed under trademark designation of "Areal") used.

What is claimed is:

1. A water-absorbent resin powder composition comprising a water-absorbent resin having a cross-linked structure obtained by polymerizing a hydrophilic monomer containing acrylic acid and/or salts thereof as a main component, wherein said water-absorbent powder composition contains an organic acid and/or salts thereof and a water-absorbent resin having a carboxyl group, and said water-absorbent resin comprises particles of an average particle diameter of from 200 to 600 μm and includes not more than 10% by weight of a fraction of particles of less than 150 μm in diameter.

2. A composition according to claim 1, wherein said organic acid is at least one member selected from the group consisting of lactic acid, citric acid and tartaric acid.

3. A composition according to claim 1, wherein said water-absorbent resin composition further contains a polyamino acid and/or salts.

4. A composition according to claim 1, wherein said water-absorbent powder composition contains the organic acid (salt) and a water-absorbent resin having a carboxyl group, and a surface area of said water-absorbent resin is cross-linked with a cross-linking agent capable of reacting with carboxyl groups.

5. A composition according to claim 1, wherein the ratio of said organic acid and/or salts is from 0.005 to 8 parts by weight to 100 parts by weight of said water-absorbent resin.

6. A composition according to claim 3, wherein said polyamino acid and/or salts is at least one member selected from the group consisting of polyaspartic acid and/or salts, polyglutamic acid and/or salts, and polylysine and/or salts.

7. A composition according to claim 1, wherein said water-absorbent composition exhibits an absorption capacity without load of at least 25 g/g to physiological saline solution (0.9% by weight of aqueous sodium chloride solution) for 60 minutes, a suction power of not less than 14 g/g to physiological saline solution for 10 minutes and a suction power of at least 7 g/g to bovine blood for 10 minutes.

8. A composition according to claim 1, wherein the absorption capacity under load of 20 g/cm$^2$ (about 1.9 kPa) for 30 minutes is at least 30 ml/g to physiological saline (0.9% by weight of aqueous sodium chloride solution).

9. A composition according to claim 2, wherein the ratio of said organic acid and/or its salts is from 0.005 to 8 parts by weight to 100 parts by weight of said water-absorbent resin.

10. A composition according to claim 3, wherein the ratio of said organic acid and/or salts is from 0.005 to 8 parts by weight to 100 parts by weight of said water-absorbent resin.

11. A composition according to claim 4, wherein the ratio of said organic acid and/or salts is from 0.005 to 8 parts by weight to 100 parts by weight of said water-absorbent resin.

* * * * *